United States Patent
Yamane

(10) Patent No.: US 9,629,947 B2
(45) Date of Patent: Apr. 25, 2017

(54) EXTRACORPOREAL AXIAL FLOW BLOOD PUMP WITH DETACHABLE STATOR

(71) Applicant: NATIONAL UNIVERSITY CORPORATION KOBE UNIVERSITY, Kobe-shi, Hyogo (JP)

(72) Inventor: Takashi Yamane, Hyogo (JP)

(73) Assignee: National University Corporation Kobe University, Kobe-shi, Hyogo (JP)

( * ) Notice: Subject to any disclaimer, the term of this patent is extended or adjusted under 35 U.S.C. 154(b) by 0 days.

(21) Appl. No.: 14/759,219

(22) PCT Filed: Dec. 26, 2013

(86) PCT No.: PCT/JP2013/007660
§ 371 (c)(1),
(2) Date: Jul. 3, 2015

(87) PCT Pub. No.: WO2014/106885
PCT Pub. Date: Jul. 10, 2014

(65) Prior Publication Data
US 2015/0335803 A1    Nov. 26, 2015

(30) Foreign Application Priority Data
Jan. 7, 2013    (JP) .................. 2013-000750

(51) Int. Cl.
*A61M 1/10*    (2006.01)
*F04D 3/00*    (2006.01)
(Continued)

(52) U.S. Cl.
CPC ........ *A61M 1/1012* (2014.02); *A61M 1/1008* (2014.02); *A61M 1/1029* (2014.02);
(Continued)

(58) Field of Classification Search
CPC combination set(s) only.
See application file for complete search history.

(56) References Cited

U.S. PATENT DOCUMENTS

| 4,846,152 A | 7/1989 | Wampler et al. |
| 5,041,131 A * | 8/1991 | Nagase ................. A61F 2/2406 623/3.26 |

(Continued)

FOREIGN PATENT DOCUMENTS

| JP | 1984074390 | 4/1984 |
| JP | 2003-214374 | 7/2003 |

(Continued)

*Primary Examiner* — Kennedy Schaetzle
(74) *Attorney, Agent, or Firm* — Ogilvie Law Firm

(57) ABSTRACT

An axial flow blood pump comprises: an impeller (2) that rotates around an axis and is provided with axial flow blades on the peripheral surface thereof, a permanent magnet inside the impeller (2), and a dynamic bearing or a pivot bearing; a first casing (5) that surrounds the peripheral surface of the impeller (2) and is provided with an intake port (11); an annular fixed element (6) that generates a rotating magnetic field in the impeller (2) and can be fitted onto the outer surface of the first casing (5); an outlet port (12); a second casing (3) that is provided with guide vanes (diffusers) (31) in the inner surface thereof; and a socket member (4) that is fittably and securely mounted onto the outer peripheral surface of the second casing (3) and is provided with a joining portion that can join with the fixed element (6).

20 Claims, 8 Drawing Sheets

(51) Int. Cl.
*F04D 29/18* (2006.01)
*F04D 29/52* (2006.01)
*F04D 29/64* (2006.01)
*F04D 13/06* (2006.01)
*F04D 29/54* (2006.01)

(52) U.S. Cl.
CPC .......... *A61M 1/1031* (2014.02); *F04D 3/00* (2013.01); *F04D 13/0646* (2013.01); *F04D 29/181* (2013.01); *F04D 29/528* (2013.01); *F04D 29/648* (2013.01); *A61M 1/1013* (2014.02); *A61M 1/1017* (2014.02); *F04D 29/548* (2013.01)

(56) References Cited

U.S. PATENT DOCUMENTS

| | | | | |
|---|---|---|---|---|
| 5,205,721 | A * | 4/1993 | Isaacson | A61M 1/101 310/184 |
| 5,527,159 | A * | 6/1996 | Bozeman, Jr. | A61M 1/10 415/900 |
| 5,588,812 | A | 12/1996 | Taylor et al. | |
| 5,911,685 | A * | 6/1999 | Siess | A61M 1/101 415/900 |
| 6,210,133 | B1 * | 4/2001 | Aboul-Hosn | A61M 1/101 417/423.1 |
| 6,527,521 | B2 * | 3/2003 | Noda | F04D 3/02 415/900 |
| 8,366,599 | B2 | 2/2013 | Tansley et al. | |
| 2003/0021683 | A1 * | 1/2003 | Capone | F04D 29/047 415/220 |
| 2003/0163019 | A1 * | 8/2003 | Goldowsky | A61M 1/101 600/16 |
| 2005/0033107 | A1 * | 2/2005 | Tsubouchi | A61M 1/10 600/6 |
| 2005/0107657 | A1 * | 5/2005 | Carrier | A61M 1/101 600/16 |
| 2006/0122456 | A1 * | 6/2006 | LaRose | A61M 1/101 600/16 |
| 2006/0241335 | A1 * | 10/2006 | Benkowski | A61M 1/101 600/16 |
| 2008/0262289 | A1 | 10/2008 | Goldowsky | |
| 2008/0269880 | A1 * | 10/2008 | Jarvik | A61M 1/101 623/3.13 |
| 2008/0292478 | A1 * | 11/2008 | Baykut | A61M 1/101 417/420 |
| 2009/0112312 | A1 * | 4/2009 | LaRose | A61M 1/101 623/3.13 |
| 2009/0143635 | A1 * | 6/2009 | Benkowski | A61M 1/122 600/16 |
| 2009/0259308 | A1 * | 10/2009 | Hidaka | A61M 1/101 623/3.13 |
| 2010/0174131 | A1 * | 7/2010 | Foster | A61M 1/101 600/16 |
| 2012/0245681 | A1 | 9/2012 | Casas et al. | |
| 2014/0255176 | A1 * | 9/2014 | Bredenbreuker | F04D 15/0005 415/208.1 |

FOREIGN PATENT DOCUMENTS

| | | |
|---|---|---|
| JP | 2004-73400 | 3/2004 |
| JP | 4107886 B2 | 6/2008 |
| JP | 2008-194482 | 8/2008 |

* cited by examiner

EXTRACORPOREAL AXIAL FLOW BLOOD PUMP WITH DETACHABLE STATOR

TECHNICAL FIELD

The present invention relates to a technology of a portable axial-flow blood pump that is practicable as a blood pump for extracorporeal circulation and as an implantable blood pump in the future.

BACKGROUND ART

Conventionally, centrifugal pumps and roller pumps have been mainly used as assist pumps for extracorporeal circulation during and after cardiac operation (hereinafter "a blood pump") and as an advance preparation (bridge-to-decision) prior to an implant of long term artificial heart. (Refer to the patent literature 1, for example). There has been little necessity for saving weight of the blood pump itself because blood pumps are ordinarily operated by being placed at the side of a surgical table in an operation room or at the side of the bed in medical wards along with drive means such as drive motors in many cases.

Also, centrifugal pumps are accepted as being economical within a certain scope though they have some cost due to the usage of disposable pump heads, and they have the merit of high pressure generation even for a high flow situation. However, centrifugal pumps have problems when they are operated as portable blood pumps because the centrifugal pumps contain motor drive units that are not disposable and weigh more than 1 Kg (1.6 Kg for example).

On the other hand, roller pumps have an advantage of being economical because patient consumables are only tubes. However, it is difficult for roller pumps to be operated continuously for a long term such as more than a week due to fatigue breakdown of tubes.

Recently, durability of mechanical circulatory support pumps has been improved and the demand for artificial hearts has become intense and consequently usage of blood pumps mentioned above has increased and blood pumps which are low cost, compact, lightweight and portable are required.

Also, a configuration to place a stator at the periphery of a centrifugal pump has been conventionally known in a centrifugal pump used for a blood pump. However, there is a problem in that such a configuration makes a centrifugal pump itself larger in the diametrical direction and consequently the equipment becomes larger.

Under such circumstances, inventors have already proposed a magnetic levitation pump with small sized dynamic pressure bearings (refer to patent literature 2) in which a stator and a rotor are disposed along the axis direction and the rotor is rotatable with a magnetic levitation status. The proposed magnetic levitation pump with small size dynamic pressure bearings is equipped with an axial-flow impeller and dynamic pressure bearings, and is also equipped with a rotation axis body having permanent magnets at each end and a magnetic coupling means disposed in such a manner that said magnetic coupling means faces each end of the rotation axis body.

However, in the proposed magnetic levitation pump with dynamic pressure bearings, the magnetic coupling means was closely integrated to the pump main body and the magnetic coupling means was not easily dismounted from the pump main body. After the proposed magnetic levitation pump is used as auxiliary pump for internal circulation, it is currently difficult to use the magnetic levitation pump for other operations or other patients, from a hygiene perspective and also a perspective of blood clot formation, and the situation is that the magnetic levitation pump is disposed of after it has been used once.

Also, an implantable axial-flow blood pump containing a blood immersed axle bearing is known as one type of axial-flow pump. (Refer to the patent literature 3) In the configuration of the axial-flow blood pump disclosed in the patent literature 3, a cup 34 equipped with a stator impeller 30 and a cup 54 equipped with an exit stator impeller 48 are attached to anterior and posterior balls (38, 52) of a pump rotor 20 that is housed in a housing 12. The stator impeller 30 and the exit stator impeller 48 fit the inner periphery of the housing 12 to function as a bearing for the pump rotor 20. The pump rotor is equipped with a rotor blade 44 that accelerates blood flow and the blood flow velocity is lowered by an exit stator blade 48 and the rotation is stopped to drain the blood toward the exit 18. Note that the motor stator 22 is secured in such a manner that the motor stator 22 encircles the periphery of the stator tube 23 that is secured on the inside of the housing 12. (Refer to FIGS. 1 to 4; paragraphs 0013 to 0016 of the patent literature 3)

As has been mentioned above, it is observed in the configuration of the axial-flow blood pump disclosed in the patent literature 3 that the structure of the housing 12 is complicated and de-installation of the motor stator 22 is accordingly difficult.

Currently, the technology of implantable auxiliary artificial hearts made of Titanium is well established. However, many patients exist to whom auxiliary artificial hearts cannot be applied. Those patients are children with antithrombogenicity at a low blood flow rate and also elderly people whose heart transplant registration is not permitted. Children require blood pumps that are extremely compact and lightweight, with antithrombogenicity at a low blood flow, and for these reasons the pump has to be selected not from transplantable types but from extracorporeal types and consequently axial-flow pumps that can adopt long and thin motor magnets and can be made small are befitted. Also for elderly people, auxiliary artificial hearts must be made of polymer materials, not of metals, and must have a structure that realizes a pump with a reusable driving portion, in consideration of the cost.

PRIOR ART

[Patent literature 1] JPA 2004-073400
[Patent literature 2] JPA 2003-214374
[Patent literature 3] JPA 2008-194482

OUTLINE OF THE INVENTION

Problems to be Solved by the Invention

In view of the situation mentioned above, the present invention aims to provide an axial-flow blood pump having a stator and a power supply equipment that are removable in an easy manner and in which parts excluding the stator and the power supply equipment are disposable.

Means to Solve the Objects

In order to accomplish the objective mentioned above, the axial-flow blood pump based on the first viewpoint of the present invention is configured to be equipped with a first cylindrically shaped casing for blood flows therein, a second casing with guide vanes (also referred to as a diffuser)

arranged at the inner peripheral surface thereof, an impeller (also referred to as a rotor) that includes an axial-flow blade placed rotatably on the inside of the first casing, a cylindrical stator firmly fixed to the tube periphery of the first casing in a removable way for applying turning force to the rotor, and a joint for enabling free assembling and disassembling of the first casing and the second casing.

With such a configuration, the stator and the power supply equipment are easily disassembled from the casings. Also the pump members in contact with blood, namely parts excluding the stator and the power supply equipment, can be disposable.

Here, the shape of the stator can be freely selected so long as the stator shape concerned can be firmly attached to the peripheral portion of the first cylindrical casing by any one of fitting, engagement or screwing in a detachable manner. Namely, the cross-sectional shape orthogonally intersecting the longitudinal direction of the inner periphery of the stator can be freely selected among a circle or polygons so long as it is firmly attached to the outer periphery of the first cylindrical casing in a detachable manner. Accordingly, the shape of the outer periphery of the stator is not specifically limited.

However, it is preferable that the stator has a cylindrical shape for achieving portability, convenience and miniaturization. By making the stator shape cylindrical, the stator can be firmly attached by fitting to the peripheral surface of the first casing and the stator can be made to be detachable from the first casing. Namely, disassembling and assembling of the axial-flow blood pump can be easily performed by dismantling the stator from the first casing or by inserting the first casing into the stator like a ring, respectively.

Also, guide vanes are installed at the inner peripheral surface of the second casing in order to restore rectilinear liquid flow to the swirling liquid flow caused by the rotation of the impeller.

Here, it is preferable, in the axial-flow blood pump according to the present invention, that the first casing is a tapered shape tube expanding from the inlet, the second casing is a tapered shape tube expanding from the discharge opening, the impeller has a tapered shape to be storable on the inside of the first casing and the inner periphery of the stator has a tapered shape.

The inner periphery of the stator has a tapered shape so that the stator can be attached more firmly to the outer periphery of the first casing, which includes a tube of a taper shape, by either fitting or screwing in a detachable manner. The stator with its tapered inner periphery can be attached easily and firmly to the outer periphery of the casing and the stator can be made to be detachable from the casing in an easier manner, in comparison to a case in which the inner periphery of a stator is not tapered. Namely, easier assembling and disassembling become available, such as allowing the stator to be dismantled from the casing or inserted to the casing more easily.

Also, it is preferable that the joining portion is firmly fixed to the outer periphery of the second casing by any one of fitting, engagement or screwing, and is composed of a socket member fittable to the stator, and an O ring is provided at the junction of the first casing and the second casing. For example, the shape of the socket member at the joining portion can be in any form as long as the joining portion can be firmly fixed by fitting to the outer periphery of the second cylindrical casing, namely the cross sectional shape orthogonally intersecting the longitudinal direction of the inner periphery of the socket member is somewhat like a circle or polygons which provides firm fixation by fitting to the outer periphery of the second cylindrical casing, as was the case of the stator mentioned above.

It is preferable that the socket member is in a cylindrical form in order to aim for portability, convenience and miniaturization as was the case of the stator mentioned above. By making the shape of the socket member cylindrical, the socket member can be firmly fixed to the outer periphery of the second casing and furthermore, assembling and disassembling of the axial-flow pump can be easily performed by dismantling the socket member from the second casing or inserting the second casing into the socket member like a ring.

Also, airtightness at the junction can be improved by installing an O ring at the junction of the first casing and the second casing.

Also, the axial-flow blood pump based on the second viewpoint according to the present invention consists of the configuration as listed in 1) to 5) below in which the stator and the power supply equipment are detachable and reusable, and the parts excluding the stator and the power supply equipment are disposable.

1) An impeller that rotates around an axis line, the impeller being equipped with an axis-flow blade at the side face thereof and having a permanent magnet and a hydrodynamic bearing or a pivot bearing.
2) A first casing surrounding the periphery of an impeller and being equipped with an inlet.
3) A stator in a ring shape, to generate a rotating magnetic field for the impeller, and to be firmly fixable to the outer periphery of the first casing.
4) A second casing equipped with an exhaust port and guide vanes (diffuser) at the inner periphery thereof.
5) A socket member equipped with a junction that can be firmly fitted to the outer periphery of the second casing and can be joined with said stator.

According to the configuration described above, the stator and the power supply equipment can be easily detached and the parts except the stator and the power supply equipment can be disposable. Here, the power supply equipment involves either a system that draws in the electricity from the external power supply via a wall socket or a battery power source such as dry cells, including a power source cable. The power source cable here is connected to the stator and the stator can take in electric power from the external power source or a battery.

In the configuration described above, an internal bladed wheel (impeller) rotates by the magnetic force of the ring-shaped stator. Such a rotation power of the impeller generates a pumping power that pushes out blood from the inlet of the casing toward the outlet to form a pump. For miniaturization of the pump, an axial flow type blade is employed as the blade.

Also, the configuration 1) to 5) above enables assembling and disassembling. The stator can be detachable from the first casing like a ring because the stator is circular and can be firmly fixed by fitting to the outer periphery of the first cylindrical casing. An axial-flow blood pump with a disposable pump and a reusable motor can be realized due to the configuration in which the stator can be detached from the first casing like a ring.

The impeller that rotates around the axis is equipped with a hydrodynamic bearing or a pivot bearing. In the case of the hydrodynamic bearing, the impeller can operate by noncontact rotation and the impeller is supported in the state of rising on the inside of the first casing.

Also, in the case of the pivot bearing, a pivot bearing that supports the impeller in the rotation axis direction is established on the inside of the first casing. The form of the pivot bearing is small and bar-shaped with a small supporting width, for example, in order to make obstruction of liquid flow as small as possible.

Here, the end face far from the inlet of the first casing and the end face far from the outlet of the second facing are joined together. Accordingly, these end faces are formed to have the same shape, namely the same diameter in the case where the shape is a tube.

Also, the second casing is hard and cylindrical, and vanes that restore the liquid flow from a slewing one to a rectilinear one are connected on the inside of the second casing. The reason for setting up guide vanes (diffuser) at the inner peripheral surface of the second casing is to restore a rectilinear liquid flow to the slewing liquid flow caused by the rotation of the impeller.

Here, it is preferable that the first casing is a tapered tube expanding from the inlet, the second casing is a tapered tube expanding from the outlet, the impeller is tapered to be storable on the inside of the first casing and the inner periphery of the stator is tapered.

The inner periphery of the stator is tapered and the stator can be firmly fixed by fitting with detachability to the outer periphery of the first casing which is a tapered tube. The stator can be firmly fixed by fitting easily and securely to the outer periphery of the casing, due to its tapered inner periphery, and the stator can be made to be detachable with ease from the casing, in comparison with a cylindrical casing that is not tapered. Namely, disassembling and assembling of the pump can be more easily performed by detaching the stator from the casing or inserting the casing into the stator.

If the structure that enables the ring-shaped stator to be firmly fixed by fitting to the outer periphery of the first casing includes a tapered lateral surface of the first casing and also a tapered inner periphery of the stator, such a structure is simpler.

Furthermore, dislodgment of the impeller itself can be prevented by making the structure of the impeller tapered to be storable on the inside of the first casing.

Furthermore, in the axial-flow blood pump mentioned above, the junction has a nut structure, a locking section is arranged at the stator and a screw thread is arranged at the outer periphery of the socket member. A nut is engaged to an engaging member of the stator to be screwed with a screw thread of the socket member. By such arrangement, the first casing and the second casing can be connected easily and firmly by connecting the socket member and the stator.

And also in the axial-flow blood pump mentioned above, the junction includes a nut structure, a locking section is arranged at the socket member and a screw thread is arranged at the outer periphery of the stator. A nut is engaged to an engaging member of the socket member to be screwed with a screw thread of the stator. By such arrangement, the first casing and the second casing can be joined easily and firmly by joining the stator and the socket member.

Furthermore, in the axial-flow blood pump based on the second point of view of the present invention, an arrangement in which the first casing is a tube with a curve starting at the inlet, a pivot bearing is disposed at the inner periphery of the first casing and a stator fixing member for fixing said stator at the outer periphery of the first casing can be used.

A pivot bearing can be disposed on the inside of the inner periphery of the first casing by forming the first casing into a tube shape with its curve starting from the inlet. The shape of the pivot bearing can be a rod with a small width having the length of the internal diameter of the first casing and a pivot bearing is disposed on the inside of the inner periphery of the first casing to make effects of a hindrance against liquid flow smaller.

For the axial-flow blood pump according to the present invention mentioned above, it is preferable that the axial-flow blade is of a groove type and that the fluid that circulates along the outer surface of the impeller generates dynamic pressure between the outer surface of the impeller and the wall surface of the inner periphery of the first casing that accommodates the impeller.

Dynamic pressure can be efficiently generated between the outer surface of the impeller and the wall surface of the inner periphery of the first casing that accommodates the impeller by the fluid that circulates along the outer surface of the impeller based on the use of the axial flow blade of a groove type that does not employ an airfoil type as the axial flow blade, and the impeller can rotate without contact against the first casing.

The outer surface of the impeller becomes a hydrodynamic bearing of a multi circular arc type.

Also, in the axial-flow blood pump according to the present invention mentioned above, it is preferable that the impeller body, the first casing, the second casing and the socket member are composed of resin material selected from polycarbonate, PEEK (polyether ether ketone), acrylic resin or vinyl chloride resin, and are disposed after use.

The polymers described above are used as members of the pump parts such as the impeller main body, the casing and the socket excluding drive motors, permanent magnets and electric cables, for realizing weight saving of the axial-flow blood pump.

It should be noted that the axial-flow blood pump based on the second viewpoint according to the present invention as mentioned above preferably contains an O ring at the junction between the first casing and the second casing. It is because preparation of an O ring at the junction between the end face far from the inlet of the first casing and the end face far from the outlet of the second casing provides higher air tightness of the junction.

Effects of the Invention

According to the axial-flow blood pump of the present invention, parts such as the stator and the power supply equipment can be easily detached and the parts excluding the stator and the power supply are disposable. Also, it is effective in making the blood flow pump miniaturized and weight reduced based on the employment of hard polymers as the pump member excluding the stator and the power supply equipment and accordingly making the axial flow blood pump portable.

BEST MODE FOR CARRYING OUT THE INVENTION

Below, the modes for carrying out the present invention will be explained in detail by referencing figures. Note that the range of the present invention is not limited to the following embodiments and figures but many changes and transformation can be applicable.

Embodiment 1

Figure 1:
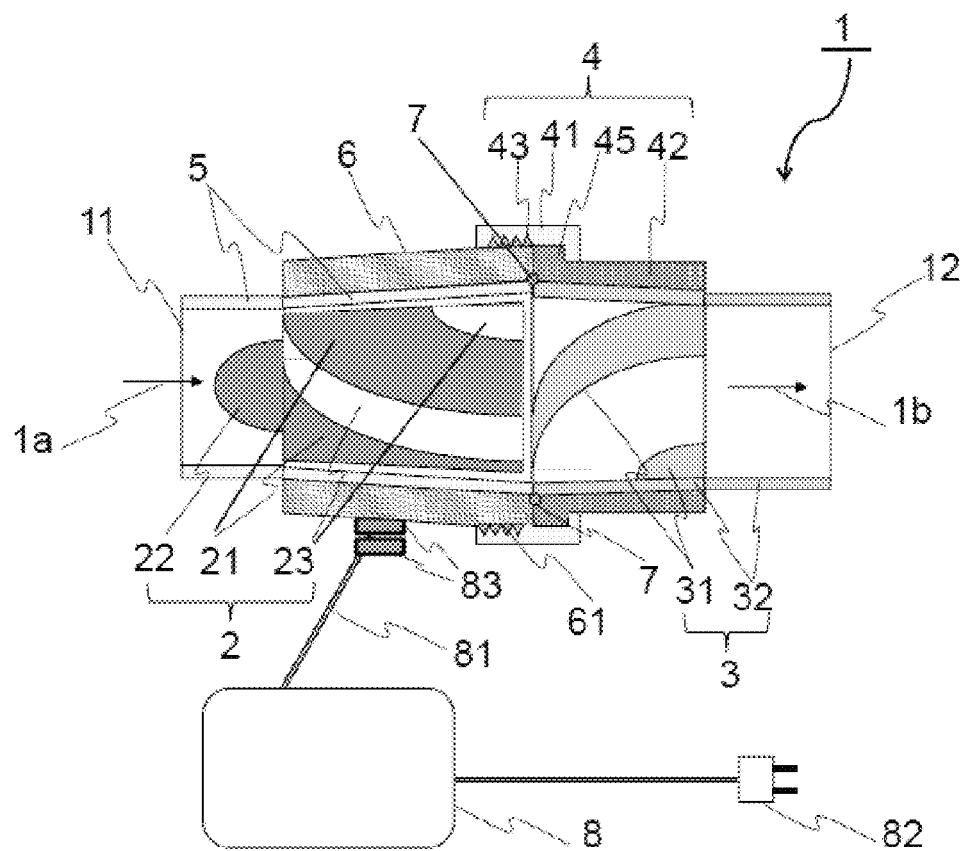
FIG. 1 An explanatory figure of the axial-flow blood pump structure according to the embodiment 1

The structure of the axial-flow blood pump according to the embodiment 1 is explained by referencing FIG. 1. The axial-flow blood pump according to the embodiment 1 consists of the following configurations 1) to 5).

1) An impeller 2 that rotates around the axis, being equipped with an axial blade 21 at the outer peripheral side face thereof and a permanent magnet and a dynamic pressure bearing 22 on the inside thereof
2) A cylindrical first casing 5 encircling the side face of the impeller 2, equipped with an inlet 11
3) A ring shaped stator capable of being fixed by fitting to the outer periphery of the first casing and capable of generating rotational magnetic field around the impeller 2
4) A cylindrical second casing 3 having an outlet 12 and guide vanes (diffuser) at the inner peripheral surface thereof
5) A cylindrical socket member 4 to be adhered by fitting to the outer periphery of the cylindrical second casing 3 and also to be equipped with a junction portion capable of being joined to a ring shaped stator 6

Symbols 1a and 1b in FIG. 1 represent the direction of the blood flow. The end face opposite the inlet 11 of the first casing 5 placed at the upstream region and the end face opposite the outlet 12 of the second casing 3 placed at the downstream region are joined. These end surfaces are made to have the same internal diameter. The sealing quality of the junction is elevated by setting up an O ring 7 made of silicone rubber at the junction portion.

Vanes (diffuser) that restores the rectilinear blood flow from the slewing blood flow is joined on the inside of the second casing 3. Slewing is caused by the rotation of the impeller 2.

Both the first casing 5 and the second casing 3 are cylindrical and are tapered in a gentle manner. Namely, the first casing 5 is a tapered tube extending from the inlet 11 and the second casing 3 is a tapered tube extending from the outlet 12 as shown in FIG. 1. The impeller 2 has a tapered shape storable on the inside of the first casing 5. Further, the stator 6 constitutes a ring shape and the inner periphery thereof is tapered. The tapered shape of impeller 2 prevents the impeller from falling out of the inside of the first casing 5.

Figure 2:
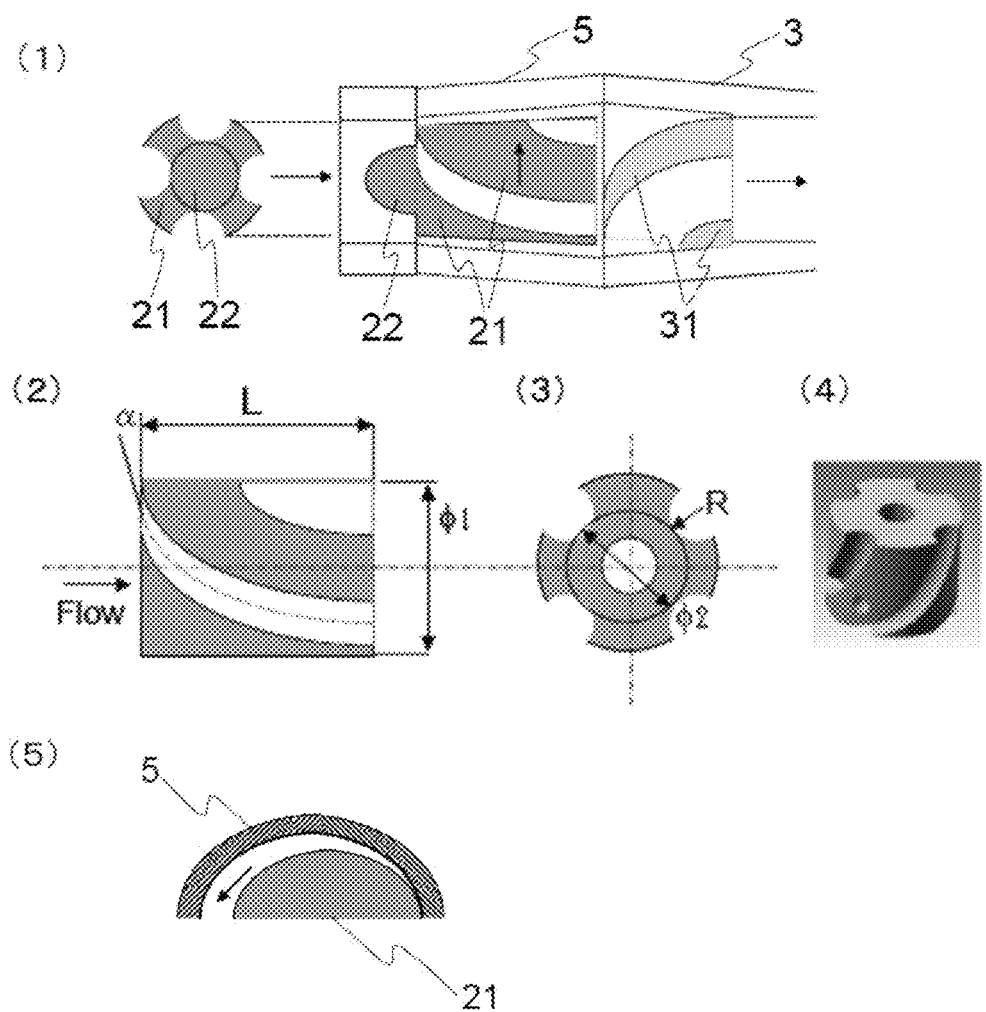
FIG. 2 An explanatory figure of the impeller of the axial-flow pump according to the embodiment 1

The first casing 5 and the second casing 3 are constituted of rigid polymer. The impeller 2 on the inside of the first casing 5 is equipped with a grooved axial-flow blade as shown in FIG. 2 (1). Although an axial-flow pump in general has a structure including a blade, the axial-flow blood pump according to the present invention includes an grooved axial-flow blade having an axial-flow fluid channel on the inside of the cylindrical first casing 5 due to the necessity to secure a large surface area for the purpose of using a hydrodynamic bearing in a combined usage. As is shown in FIGS. 2 (2) and (3), the impeller 2 is designed to gain angular momentum with enough pressure even under low velocity considering the internal diameter of the first casing 5 when designing the impeller 2 (design of geometry parameters of $\phi 1$, $\phi 2$, $\alpha$, R). In the embodiment 1, an impeller with an exterior as shown in FIG. 2 (4) is used. The dynamic bearing of the impeller 2 is a dynamic bearing of multi arcs (4 arcs in the case of FIG. 2) (refer to FIG. 2 (1)) and each arc is inclined so that the gap with the interior of the first casing 5 expands in the advancing direction (the direction of the arrow in FIG. 2 (5)).

Also, the inner periphery of the ring shaped stator 6 is tapered and is fixed by fitting to the outer periphery of the first casing 5 that is a tapered tube, in a detachable manner. The stator 6 and the first casing 5 can be securely fixed by fitting at the position determined uniquely by the inner diameter of the stator 6 and the outer diameter of the first casing 5 due to the fact that the outer periphery of the first casing 5 and the inner periphery of the stator 6 are both tapered.

Also, the inner periphery of the socket member 4 is made to be tapered and is fixed by fitting to the outer periphery of the casing 3 with detachability. The socket member 4 and the second casing 3 can be securely fixed by fitting at the position determined uniquely by the inner diameter of the socket member 4 and outer diameter of the second casing 3 due to the fact that the outer periphery of the second casing 3 and the inner periphery of the socket member 4 are both tapered.

The socket member 4 is equipped with a junction that joins with the ring shaped stator 6. The junction is nut structured, the socket member is equipped with a locking portion 45 and a screw thread 61 is disposed at the outer periphery of the stator 6. A box nut 41 has a screw groove 41 that is engaged with the locking section of the socket member 4 and is screwed together with the screw mount 61 of the stator 6. Thus, the stator 6 and the socket member 4 are securely joined and the first casing 5 and the second casing 3 are joined.

Figure 3:
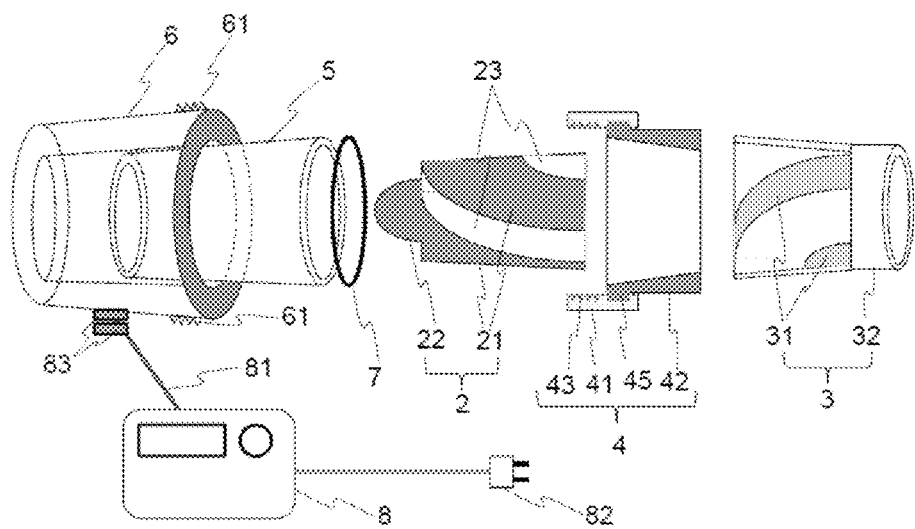
FIG. 3 An exploded schematic diagram of the axial-flow blood pump according to the embodiment 1

FIG. 3 shows an exploded schematic diagram of the axial-flow blood pump according to the embodiment 1.

The stator 6 described in 3) above and the power supply equipment (8, 81, 82) for supplying electric power to the stator 6 are connected by the connector 83 and these are detachable from the main body of the axial-flow pump and recyclable, and parts (the impeller 2, the first casing 5, the socket member 4, the second casing 3, the O ring 7 and the guide vanes (diffuser) 31) excluding the stator 6 and the power supply equipment (8, 81, 82 and 83) can be disposed of after use. The impeller 2 and the socket member 4 are also made of rigid polymer such as poly carbonate and PEEK in the same manner as for the first casing 5 and the second casing 3. The stator 6 is made of stainless steel or ferrite core.

Note that a locking section can be disposed at the stator 6 and a screw thread 44 can be disposed at the outer peripheral edge of the socket member 4 for the junction structure of the stator 6 and the socket member 4 described above as shown in FIG. 4. It is so arranged that the box nut 41 can be engaged with the locking section 62 of the stator 6 and can be screwed with the screw thread 44 of the socket member 4. By such arrangement, the stator 6 and the socket member 4 are joined and the first casing 5 and the second casing 3 are joined.

It can be acceptably arranged that a locking section is disposed at the outer peripheral part of the cylindrical second casing 3 and a screw thread 61 is disposed at the outer periphery of the stator 6 to be engaged with the box nut 41 having the groove 43 with the locking section of the outer periphery of the second casing 3 and to be screw-fitted with the screw thread 61 of the stator 6 without using the socket member 4 described in 5) above, to join the first casing 5 and the second casing 3.

Similarly, it can be acceptably arranged that a locking section 62 is disposed at the stator 6 and a screw thread is disposed at the outer periphery of the cylindrical second casing 3 without socket member 4 as described in 5) above. It is acceptable that the first casing 5 and the second casing 3 are joined by the locking of the box nut 41 having the groove 43 with the locking portion of the stator 6 and by the screwing of the box nut 41 having the groove 43 to the screw thread of the outer periphery of the second casing 3.

Next, the heat-capacity curve of the axial-flow blood pump according to the embodiment 1 is explained.

With regard to the groove type axial-flow blade impeller (hereinafter "groove type impeller") of the axial-flow blood pump, the heat-capacity curve of the groove type impeller is compared with that of the air foil type impeller as a comparative example.

In the comparative experiment, a closed circuit was formed by the impeller and a soft reservoir was structured by using a vinyl chloride tube of 15 mm inner diameter D and using ordinary tap-water, to measure fluid pressures at 2 points in upstream and downstream, respectively and a flow rate at 1 point.

Figure 10:
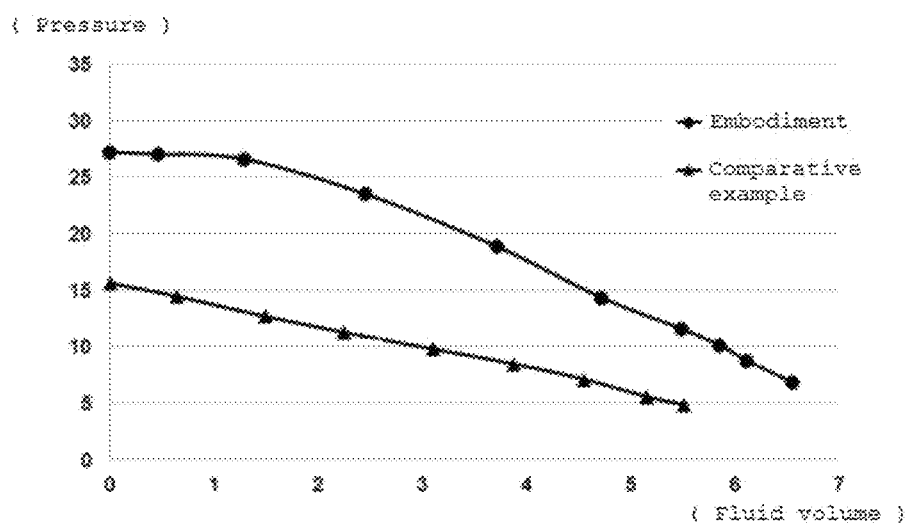
FIG. 10 A lifting height curve of the pump

The heat-capacity curve is shown in FIG. 10. Note that the pressure needs to be multiplied by 1.056 to convert to that of blood because the density value remains at that of water. When a comparison is made under the common condition of the rotation number at 12500 rpm and the fluid volume at 5 liters/minute, the generated pressure of the comparative example (air foil type impeller) is 6 k Pa and that of the embodiment (groove type impeller) is 13 k Pa, it is consequently known that two times higher pressure is generated by the groove type impeller than that of the comparison example (air foil type impeller) at the same rotation number. Conversely, even a lower rotational number sufficient generation of the predetermined pressure and improvement of hemolytic property can be expected. It is known that the hemolytic property was improved by 20% when comparison is made between the embodiment (the groove type impeller) where the rotation number was 12500 rpm and the peripheral velocity was 9.8 m/s corresponding to the pressure of 100 mm Hg and the comparative example (air foil type impeller) where the rotation number was 15000 rpm and the peripheral velocity was 11.8 m/s.

For the axial-flow blood pump according to the embodiment 1, the pump portion weighs less than 200 g and the whole weight of the pump system including the power supply equipment 8 weighs less than 400 g and the axial-flow blood pump here is about ¼ the weight of the current centrifugal pump.

Embodiment 2

Figure 5:
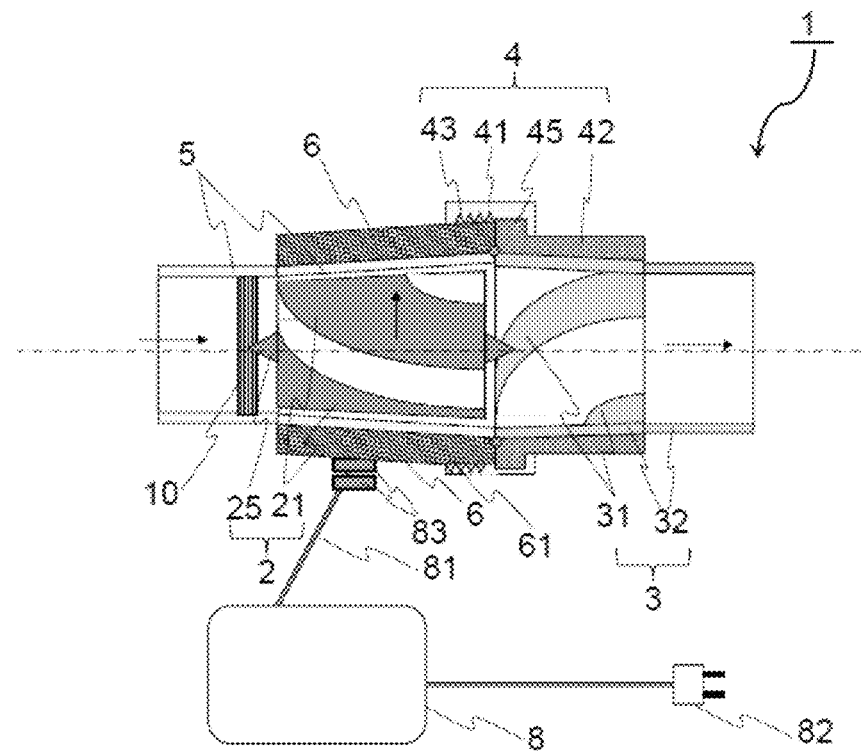
FIG. 5 An explanatory figure of the axial-flow blood pump structure according to the embodiment 2

FIG. 5 shows the structure of the axial-flow blood pump according to the embodiment 2. The axial-blood pump according to the embodiment 2 consists of the construction 2-1) to 2-5) as described below.

2-1) an impeller that rotates around the axis line having an axial-flow blade 21 at the peripheral side face thereof, and a permanent magnet and a pivot axis 25 on the inside thereof
2-2) a first cylindrical casing 5 surrounding the periphery of the impeller 2 and being equipped with an inlet 11
2-3) a stator 6, being ring shaped to be fixed by fitting to the outer periphery of the first casing 5, for generating a rotating magnetic field around the impeller 2
2-4) a second cylindrical casing 3 equipped with an outlet 12 and guide vanes (diffuser) 31 at the inner periphery thereof
2-5) the cylindrical socket member 4 to be fixed by fitting to the outer periphery of the second cylindrical casing, further being equipped with a junction connectable to the ring shaped stator 6

The explanation of each component is omitted because it overlaps with the embodiment 1.

A point that differs from the embodiment 1 is that the impeller 2 is not a dynamic bearing impeller but instead is a pivot bearing impeller.

Also, the shape of the pivot axis 25 is conical.

Figure 6:
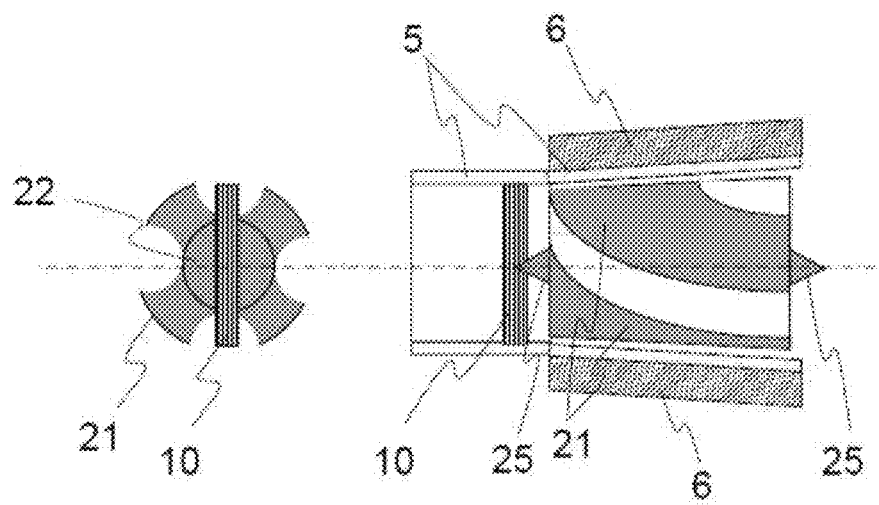
FIG. 6 An explanatory figure of the pivot bearing of the axial-flow blood pump according to the embodiment 2

As is shown in FIG. 6, with regard to the pivot bearing according to the embodiment 2, the pivot bearing 10 that supports the impeller 2 in the rotation axis direction is formed on the inside of the first casing 5. The pivot bearing 10 is rod-shaped with a small width and a length equal to the internal diameter of the first casing 5 in order to make the hindrance to the blood flow on the inside of the first casing 5 as small as possible.

Figure 4:
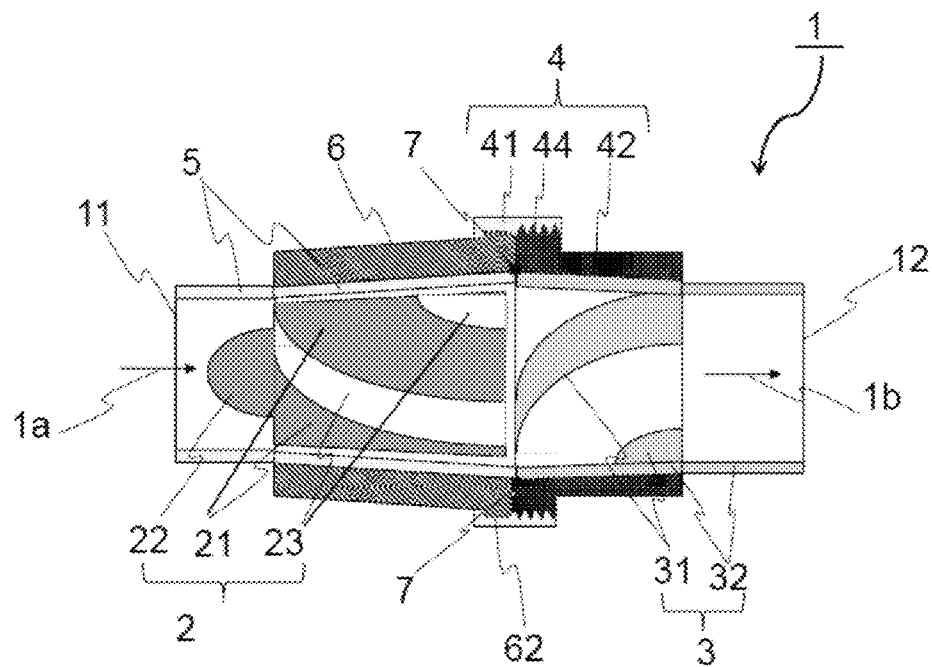
FIG. 4 An explanatory figure of the other nut structure of the axial-flow blood pump according to the embodiment 1

Note that a locking section may be provided to the stator 6 and a screw thread 44 may be provided at the outer peripheral surface of the socket member 4, as shown in FIG. 4, for constituting the structure of the junction between the stator 6 and the socket member 4. The first casing 5 and the second casing 3 may be joined by joining the stator 6 and the socket member 4 in a manner in which a box nut 41 is engaged with the locking section 62 of the stator 6 and screwed to the screw thread 44 of the socket member 4.

Embodiment 3

Figure 7:
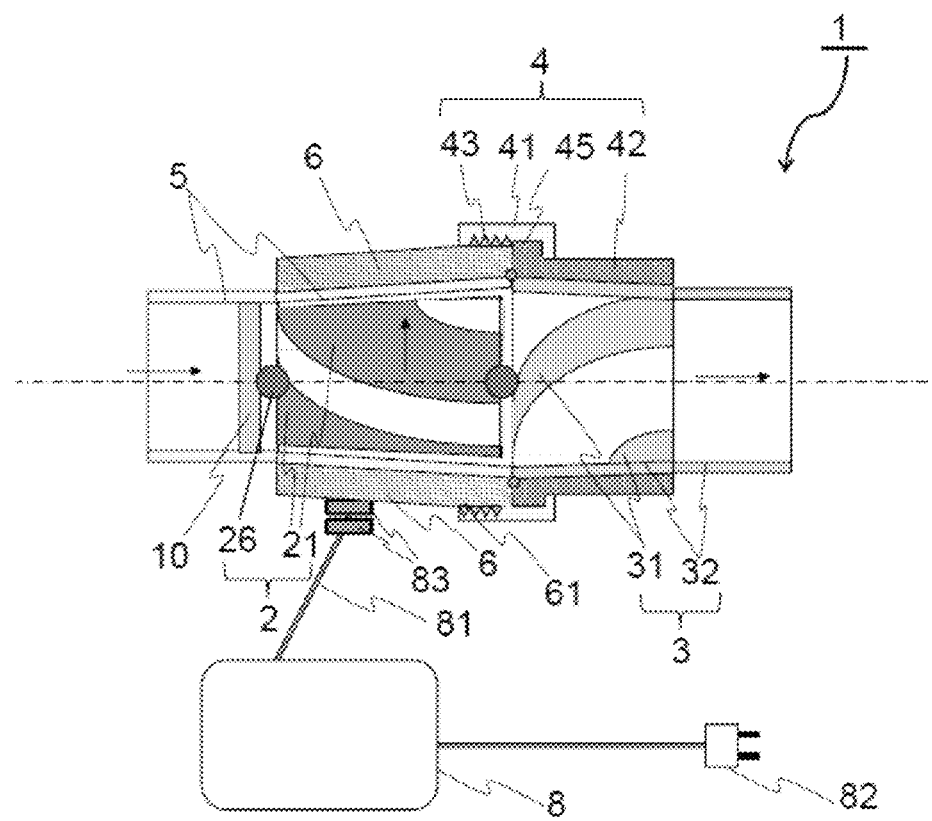
FIG. 7 An explanatory figure of the axial-flow blood pump structure according to the embodiment 3

FIG. 7 shows the structure of the axial-flow blood pump according to the embodiment 3. In the axial flow blood pump according to the embodiment 3, the shape of the pivot axis is spherical while the shape of the pivot axis in the axis-flow blood pump according to the embodiment 2 is conical. The shape of the pivot bearing 10 is the same as that in the embodiment 2 however, the shape of the pivot bearing is made to be spherical.

Figure 8:
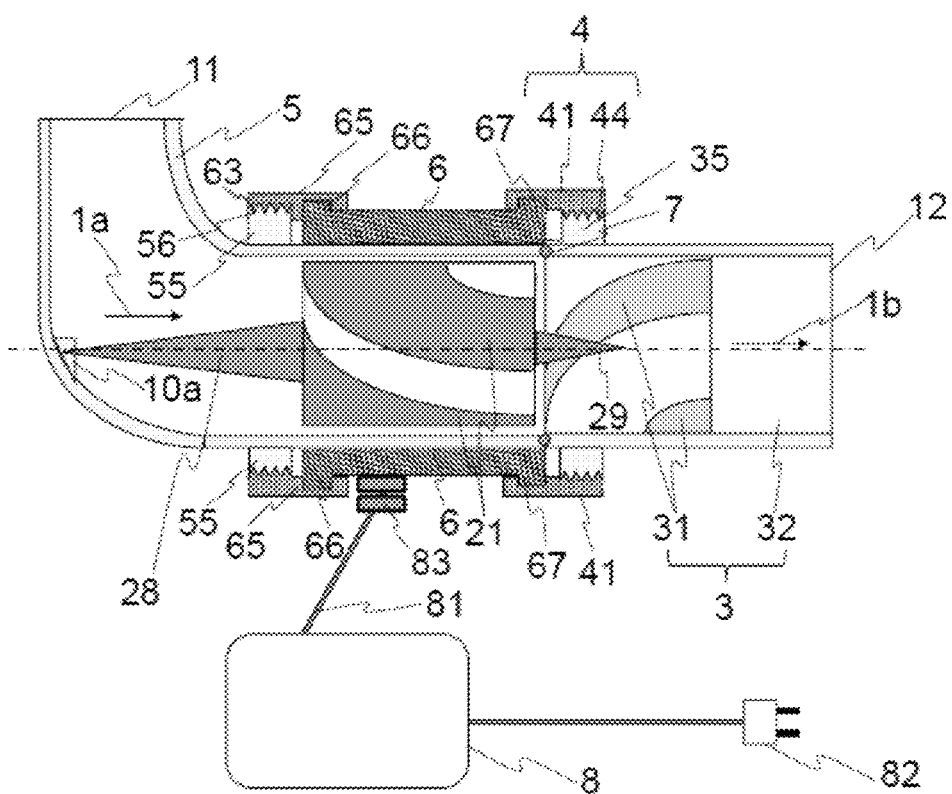
FIG. 8 An explanatory figure of the axial-flow blood pump structure according to the embodiment 4 (1)

FIG. 8 shows the structure of the axial-flow blood pump according to the embodiment 4. In the axial-flow blood pump in the embodiment 4, the first casing 5 is tube shaped, the tube being curved starting from the inlet 11. As was described in the axial-flow blood pump according to the embodiment 2, a pivot bearing 10a is disposed at the inner periphery of the first casing 5 and a stator fixing member 55 for fixing the stator 6 is disposed at the outer periphery of the first casing 5.

In the case of the embodiment 4, the shapes of the first casing 5 and the second casing 3 are not tapered. The inner periphery of the stator 6 is also not tapered. Because the first casing 5 is tube shaped curved from the inlet 11, the stator 6 is mounted or dismounted from the edge opposite the inlet 11 in the first casing 5.

As is shown in FIG. 8, a stator fixing member 55 is installed at the outer periphery of the first casing 5, and the screw thread 56 thereof is screwed to the groove 63 of the box nut. The box nut 65 is fitted with the protrusion like the locking section 66 of the stator 6. By such arrangement, the stator 6 is firmly fixed to the outer periphery of the first casing 5.

Also, a locking section 67 is installed at the stator 6, a locking section 35 having a screw thread is installed at the outer periphery of the cylindrical second casing 3, a box nut 41 is engaged with the locking section 67 of the stator 6 and the screw thread of the locking section 35 installed at the outer periphery of the second casing 3 is screwed to the screw thread 44, thus the first casing 5 and the second casing 3 are joined.

Note that joining of the first casing 5 and the second casing 3 by installing a locking section 35 at the outer periphery of the cylindrical second casing 3, installing a screw thread at the outer periphery of the stator 6, the box nut 41 having screw groove being engaged with the locking section at the outer periphery of the second casing 3 and being screwed to the screw thread of the stator 6, is acceptable.

Figure 9:
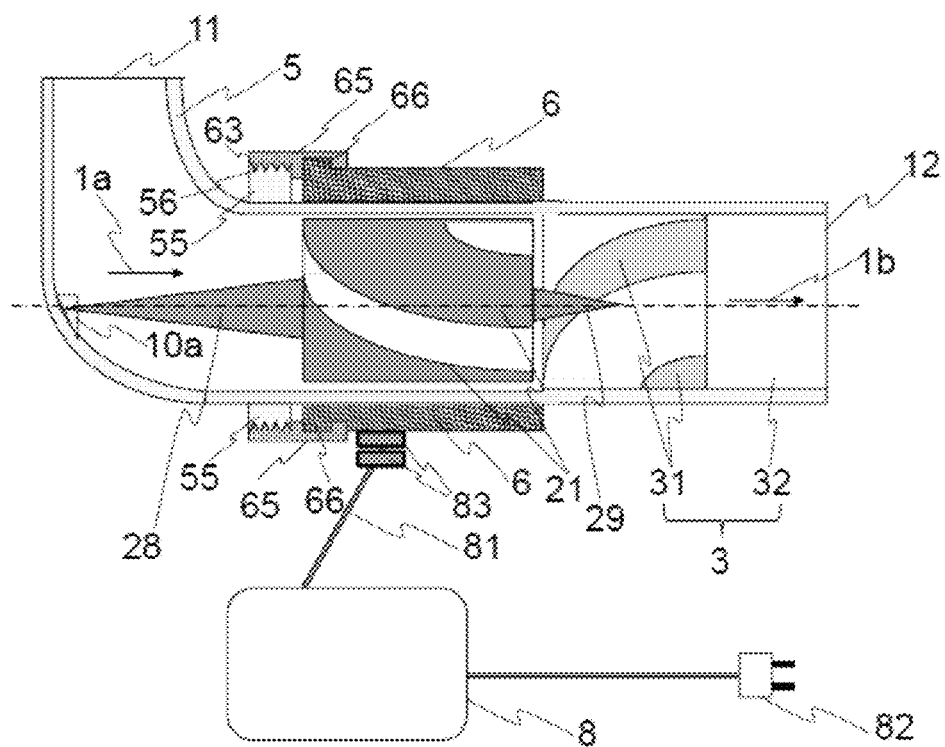
FIG. 9 An explanatory figure of the axial-flow blood pump structure according to the embodiment 4 (2)

Also, the first casing 5 and the second casing 3 both in cylindrical form with the same diameter can be integrally molded in advance, not molded by respective member, as shown in FIG. 9. This case may include a stator fixation member 55 being installed at the outer periphery of the first casing 5, the screw thread 56 and the screw groove 63 of the box nut 65 being screwed together and further being engaged with the locking section 66 protruding out of the stator 6 by the box nut 65 and consequently the stator 6 being fixed to the outer periphery of the first casing 5.

In this case, inserting and pulling out of the stator 6 is done at the edge of the second casing 3 that constitutes a part of the integral mold of the first casing 5 and the second casing 3. Therefore, the first casing 5 and the second casing 3 are both cylindrical having the same diameter and are not tapered.

INDUSTRIAL APPLICABILITY

Figure 11:
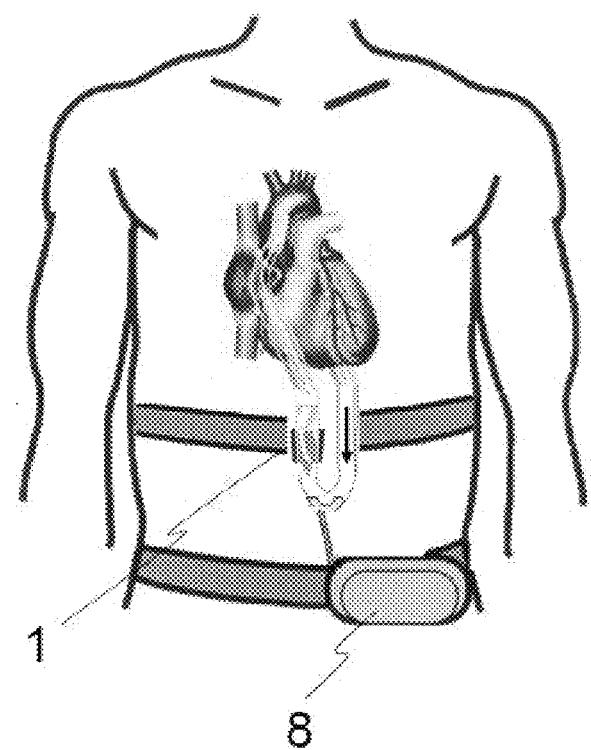
FIG. 11 A conceptual diagram of the axial-flow blood pump extracorporeally installed

The axial-flow blood pump according to the present invention is useful as a circulation assistance pump conducted as a bridge before implantation of a long term artificial heart. For example, as is shown in FIG. 11, the axial-flow blood pump 1 according to the present invention is installed in an extracorporeal environment and is used by continuously supplying electric power from the power supply equipment 8 attached to a belt worn around the waist. Note that FIG. 11 shows a circumstance in which the axial-flow blood pump 1 according to the present invention is used as an auxiliary of the left heart.

DESCRIPTION OF SYMBOLS

1 Axial-flow blood pump
1a, 1b blood flow directions
2 Impeller
3 Second casing
4 Socket member
5 First casing
6 Stator (motor stator)
7 O ring
8 Electric power supply equipment
10, 10a Pivot bearings
11 Inlet
12 Outlet
21 Axial-flow blade
22 Dynamic pressure bearing
23 Groove
25, 26, 28, 29 Pivot axis
31 Guide vanes (diffuser)
35, 45, 62, 66, 67 Locking section
41, 65 Box nut
42 Socket
43, 63 Screw thread
44, 56, 61 Screw groove
55 Fixing member for stator
81 Electric wire cable
82 Consent
83 Connector

What is claimed is:

1. An extracorporeal axial-flow blood pump, comprising:
    a first casing having a cylindrical form which permits blood flow therein;
    a second casing, joining the first casing, the second casing having blood flow guide vanes installed at an inner peripheral surface thereof;
    an axial-flow impeller disposed to be freely rotatable on the inside of the first casing in a blood flow;
    a detachable stator fixed detachably to an outer peripheral surface of the first casing in a position for adding rotational power to said impeller without the stator contacting the blood flow, the stator comprising a one-piece cylindrical ring which detachably surrounds a circumference of the first casing; and
    wherein the first casing, second casing, and impeller are disposable and the detachable stator is reusable.

2. An axial-flow blood pump as set forth in claim 1, further comprising:
    a joint for joining the first casing and the second casing with free assembling and disassembling.

3. An axial-flow blood pump as set forth in claim 2, wherein:
    said joint comprises a socket member joinable to the outer peripheral surface of the first casing and also joinable to said detachable stator; and
    an O ring is disposed at the junction of the first casing and the second casing.

4. An axial-flow blood pump as set forth in claim 3, wherein:
    said junction has a nut structure;
    said detachable stator is equipped with a locking section;
    said socket member is equipped with a screw thread at an outer peripheral surface thereof; and
    the first casing and the second casing are joined by joining said detachable stator and said socket member by having said detachable stator engaged with said locking section and having said socket member screwed to said screw thread by a nut.

5. An axial-flow blood pump as set forth in claim 3, wherein:
    said junction has a nut structure;
    said socket member is equipped with a locking section; and
    an outer peripheral surface of said detachable stator is equipped with a screw thread; and
    the first casing and the second casing are joined by joining said detachable stator and said socket member by having said socket member engaged by a nut which engages said locking section and said screw thread of the detachable stator.

6. An axial-flow blood pump as set forth in claim 3, wherein:

the first casing has a tube shape for curved blood flow from the inlet;

the first casing has a pivot bearing at an internal peripheral surface thereof; and the first casing has a fixing member for fixing said detachable stator at the outer peripheral surface of said first casing.

7. An axial-flow blood pump as set forth in claim 3, wherein:

a main body of said impeller, the first casing, the second casing and said socket member are disposable after use and comprise a resin selected from one or more of the following: poly-carbonated, polyether ether ketone, acrylic resin, or vinyl chloride resin.

8. An axial-flow blood pump as set forth in claim 1, wherein:

said axial-flow blade is of a groove type; and in operation a dynamic pressure is generated between an outer peripheral surface of said impeller and a wall surface of an inner periphery of the first casing by fluid circulating past the outer peripheral surface of said impeller.

9. An extracorporeal axial-flow blood pump, comprising:

a first casing having a cylindrical form which permits blood flow therein;

a second casing, joining the first casing, the second casing having blood flow guide vanes installed at an inner peripheral surface thereof;

an axial-flow impeller disposed to be freely rotatable on the inside of the first casing in a blood flow;

a detachable stator fixed detachably to an outer peripheral surface of the first casing in a position for adding rotational power to said impeller without the stator contacting the blood flow, the stator comprising a one-piece cylindrical ring having a tapered inner periphery which detachably surrounds a tapered annulus of the first casing;

the first casing comprising a tapered tube expanding from an inlet;

the second casing comprising a tapered tube expanding from an outlet;

said impeller being tapered to be storable on the inside of the first casing;

wherein the first casing, second casing, and impeller are disposable and the detachable stator is reusable.

10. An axial-flow blood pump as set forth in claim 9, further comprising:

a joint for joining the first casing and the second casing with free assembling and disassembling.

11. An axial-flow blood pump as set forth in claim 10, wherein:

said joint comprises a socket member joinable to the outer peripheral surface of the first casing and also joinable to said detachable stator; and an O ring is disposed at the junction of the first casing and the second casing.

12. An axial-flow blood pump as set forth in claim 11, wherein:

said junction has a nut structure;

said detachable stator is equipped with a locking section;

said socket member is equipped with a screw thread at an outer peripheral surface thereof; and the first casing and the second casing are joined by joining said detachable stator and said socket member by having said detachable stator engaged with said locking section and having said socket member screwed to said screw thread by a nut.

13. An axial-flow blood pump as set forth in claim 9, wherein:

said axial-flow blade is of a groove type; and in operation a dynamic pressure is generated between an outer peripheral surface of said impeller and a wall surface of an inner periphery of the first casing by fluid circulating past the outer peripheral surface of said impeller.

14. An extracorporeal axial-flow blood pump, comprising:

an impeller rotatable around an axis line, said impeller comprising an axis-flow blade disposed at a periphery side face thereof and a permanent magnet and a hydrodynamic bearing or a pivot bearing on an end thereof;

a first casing surrounding the side face of the impeller and equipped with an inlet for a blood flow;

a detachable stator, positioned for generating a rotational magnetic field in the impeller, said detachable stator having a solid portion which is ring shaped and shaped to be fixed to an outer periphery of the first casing outside the blood flow;

a second casing equipped with an outlet for the blood flow and having guide vanes at an inner periphery surface thereof;

a socket member equipped with a junction shaped for being fixed to the outer periphery of the second casing and also joinable to the stator;

said detachable stator being removable from the pump and reusable with another impeller and other casings; and parts of said pump excluding said detachable stator being disposable.

15. An axial-flow blood pump as set forth in claim 14, wherein:

the first casing comprises a taper shaped tube expanding from the inlet;

the second casing comprises a taper shaped tube expanding from the outlet;

said impeller comprises a taper shaped portion storable on the inside of the first casing; and an inner periphery surface of said stator is tapered.

16. An axial-flow blood pump as set forth in claim 14, wherein:

said junction has a nut structure;

said detachable stator is equipped with a locking section;

said socket member is equipped with a screw thread at an outer peripheral surface thereof; and the first casing and the second casing are joined by joining said detachable stator and said socket member by having said detachable stator engaged with said locking section and having said socket member screwed to said screw thread by a nut.

17. An axial-flow blood pump as set forth in claim 14, wherein:

said junction has a nut structure;

said socket member is equipped with a locking section; and an outer peripheral surface of said detachable stator is equipped with a screw thread; and the first casing and the second casing are joined by joining said detachable stator and said socket member by having said socket member engaged by a nut which engages said locking section and said screw thread of the detachable stator.

18. An axial-flow blood pump as set forth in claim 14, wherein:

the first casing has a tube shape for curved blood flow from the inlet;

the first casing has said pivot bearing at an internal peripheral surface thereof; and the first casing has a fixing member for fixing said detachable stator at an outer peripheral surface of said first casing.

19. An axial-flow blood pump as set forth in claim 14, wherein:

said axial-flow blade is of a groove type; and in operation a dynamic pressure is generated between an outer peripheral surface of said impeller and a wall surface of an inner periphery of the first casing by fluid circulating past the outer peripheral surface of said impeller.

20. An axial-flow blood pump as set forth in claim 14, wherein:

a main body of said impeller, the first casing, the second casing and said socket member are disposable after use and comprise a resin selected from one or more of the following: poly-carbonated, polyether ether ketone, acrylic resin, or vinyl chloride resin.

\* \* \* \* \*